(12) United States Patent
Hedley et al.

(10) Patent No.: US 7,837,737 B2
(45) Date of Patent: Nov. 23, 2010

(54) FEMORAL PROSTHESIS

(75) Inventors: Anthony K. Hedley, Paradise Valley, AZ (US); Damon Servidio, Towaco, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 193 days.

(21) Appl. No.: 11/504,446

(22) Filed: Aug. 15, 2006

(65) Prior Publication Data

US 2008/0140214 A1 Jun. 12, 2008

(51) Int. Cl.
*A61F 2/38* (2006.01)
(52) U.S. Cl. .............. 623/20.35; 623/20.14; 623/20.21; 623/20.36
(58) Field of Classification Search .............. 623/20.35, 623/20.36, 20.14, 20.21; 206/363
See application file for complete search history.

(56) References Cited

U.S. PATENT DOCUMENTS

| | | | |
|---|---|---|---|
| 3,924,277 A | 12/1975 | Freeman et al. | |
| 4,731,086 A | 3/1988 | Whiteside et al. | |
| 4,822,365 A | 4/1989 | Walker et al. | |
| 4,936,847 A | 6/1990 | Manginelli | |
| 4,944,756 A | 7/1990 | Kenna | |
| 4,950,298 A | 8/1990 | Gustilo et al. | |
| 4,985,037 A * | 1/1991 | Petersen ................... | 623/20.15 |
| 5,197,987 A | 3/1993 | Koch et al. | |
| 5,226,915 A | 7/1993 | Bertin | |
| 5,358,527 A | 10/1994 | Forte | |
| 5,445,642 A * | 8/1995 | McNulty et al. .............. | 606/88 |
| 5,549,688 A | 8/1996 | Ries et al. | |
| 5,776,201 A | 7/1998 | Colleran et al. | |
| 5,800,552 A | 9/1998 | Forte | |
| 5,824,100 A | 10/1998 | Kester et al. | |
| 5,824,105 A | 10/1998 | Ries et al. | |
| 6,013,103 A | 1/2000 | Kaufman et al. | |
| 6,264,697 B1 | 7/2001 | Walker et al. | |
| 6,406,497 B2 | 6/2002 | Takei et al. | |
| 6,540,787 B2 | 4/2003 | Biegun et al. | |
| 6,589,283 B1 | 7/2003 | Metzger et al. | |
| 6,770,099 B2 | 8/2004 | Andriacchi et al. | |
| 6,893,467 B1 | 5/2005 | Bercovy et al. | |
| 6,905,513 B1 | 6/2005 | Metzger | |
| 2001/0021877 A1 | 9/2001 | Biegun et al. | |
| 2002/0010512 A1 | 1/2002 | Takei | |
| 2002/0068979 A1 | 6/2002 | Brown et al. | |
| 2003/0225458 A1 | 12/2003 | Donkers et al. | |
| 2004/0098132 A1 | 5/2004 | Andriacchi et al. | |
| 2004/0172137 A1 | 9/2004 | Blaylock et al. | |
| 2005/0246029 A1 | 11/2005 | Keller | |
| 2006/0058884 A1 | 3/2006 | Aram et al. | |

FOREIGN PATENT DOCUMENTS

DE 263135 8/1912

(Continued)

*Primary Examiner*—David Isabella
*Assistant Examiner*—Yashita Sharma
(74) *Attorney, Agent, or Firm*—Lerner, David, Littenberg, Krumholz & Mentlik, LLP

(57) ABSTRACT

A total stabilized femoral knee prosthesis is disclosed. Such prosthesis is capable of being formed with varying condyle thicknesses, and may include a stem, stabilizer box and articular surface. Methods of implanting such a prosthesis, as well as of manufacturing same are also disclosed herein.

29 Claims, 8 Drawing Sheets

FOREIGN PATENT DOCUMENTS

| | | |
|---|---|---|
| EP | 478587 | 4/1992 |
| EP | 1421920 | 5/2004 |
| FR | 2290883 | 6/1976 |
| FR | 2839642 | 11/2003 |
| GB | 2070939 | 9/1981 |
| JP | 9308642 | 12/1997 |
| WO | WO-9014806 | 12/1990 |
| WO | WO-00/19945 | 4/2000 |

\* cited by examiner

FEMORAL PROSTHESIS

BACKGROUND OF THE INVENTION

The present invention relates to a femoral prosthesis for use in replacing at least a portion of the distal femur during a surgical procedure, and more particularly, to a total stabilized knee prosthesis for use in revision surgery.

Replacement of portions of the femoral and tibial components of the knee joint has become more and more common in recent years in order to repair damaged or diseased joints. Typically, such replacement procedures include removing at least a portion of bone and introducing one or more prosthetics to restore articulating surfaces suffering from cartilage degeneration or the like. Whether performed as a total knee procedure or one in which only a portion of the knee joint is replaced (e.g.—a unicondylar procedure) such surgical procedures are very effective in alleviating pain and/or improving mobility. Nonetheless, implants commonly utilized in these replacement procedures often have a definitive life expectancy and, over time, require replacement through other procedures, such as revision procedures.

A representative revision procedure is typically performed when a previously implanted prosthesis loosens or dislocates, an infection occurs, the prosthesis experiences significant wear, or when such prosthesis is not initially properly positioned. When it is determined that a revision procedure is required, the previously implanted prosthesis is removed and a revision prosthesis is put in its place. Typically, this involves the removal of supplementary bone in addition to that which has already been removed. For example, in replacing a femoral component, a further portion of the condyles of the femur may need to be removed. When this occurs, additional thickness in the revision prosthesis (often times in the condyle portions) is required to compensate for at least some of the bone that has been lost or removed in order to maintain the anatomical relationship necessary to stabilize the new prosthesis and allow for natural movement in the knee joint. Frequently, this additional thickness is added through the use of augments or other spacer devices that are not actually part of the prosthesis. However, these augments have the tendency to create improper loading upon the prosthesis during normal knee movement. In addition, more components for use during a surgery increase the chances of operating room confusion and adds to the possibility of deadly infections from improperly sterilized instruments and prosthesis.

Therefore, there exists a need for a femoral prosthesis that can be offered in varying thicknesses, while remaining a single prosthetic that is stable, promotes proper loading and is easy to manufacture.

SUMMARY OF THE INVENTION

A first aspect of the present invention is a femoral trial prosthesis kit. In accordance with at least one embodiment, the kit includes at least a first and second femoral trial prosthesis. Each femoral trial prosthesis also preferably includes a stem, a stabilizer box connected to the stem and an articular surface connected to the stabilizer box, the articular surface including a proximal surface and a distal surface. Preferably, a distance between at least a portion of the proximal and distal surfaces of the articular surface of the first femoral trial prosthesis is less than a distance between at least a portion of the proximal and distal surfaces of the articular surface of the second femoral trial prosthesis.

In other embodiments, the stems of the first and second femoral trial prosthesis may be tapered, may include flutes and may be formed integrally or be modular with respect to the other components of each implant. The stabilizer boxes may define a box cut surface on a proximal side and a cam surface on a distal side, wherein the box cut surface includes a top bone engaging surface and two side bone engaging surfaces. Additionally, the cam surface includes a cam platform and four side walls. The kit may also include other components, such as a tibial component. The cam surface is preferably adapted to cooperate with a portion of the tibial component. Still further, the distal surface of the articular surface may include a distal articular surface, an anterior superior articular surface and a posterior superior articular surface, and the distal surfaces of the articular surfaces of the first and second trial prosthesis may be substantially similar. The proximal surface of the articular surface may include three bone engaging surfaces, including an anterior surface, a distal surface and a posterior surface. Finally, the bone engaging surfaces of the first and second trial prosthesis may be substantially similar. Thus, each prosthesis preferably fits on the same bone cuts.

Another aspect of the present invention is a method of manufacturing different thickness femoral prosthesis. Such method may include the steps of providing a first mold portion adapted for use in molding a distal portion of an articular surface of first and second prosthesis, proving a second mold portion adapted for use in molding a stem, at least three cut bone engaging surfaces, a stabilizer box, an anterior superior articular surface and a posterior superior articular surface of the first prosthesis, proving a third mold portion adapted for use in molding a stem, at least three cut bone engaging surfaces, a stabilizer box, an anterior superior articular surface and a posterior superior articular surface of the second prosthesis, engaging the first and second mold portions, molding a first prosthesis, engaging the first and third mold portions and molding a second prosthesis.

In accordance with other aspects of the above-described method, the molding steps form first and second prosthesis with tapered stems and or stems including flutes. The molding steps may also form first and second prosthesis with stabilizer boxes defining box cut surfaces and a cam surfaces, wherein the box cut surfaces each include a top bone engaging surface and two side bone engaging surfaces. Additionally, the cam surfaces each include a cam platform and four side walls. Preferably, a distance between the distal portion of the articular surface and at least one of the three cut bone engaging surfaces of the first femoral prosthesis is less than a distance between distal portion of the articular surface and at least one of the three cut bone engaging surfaces of the second femoral prosthesis.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Figure 1:
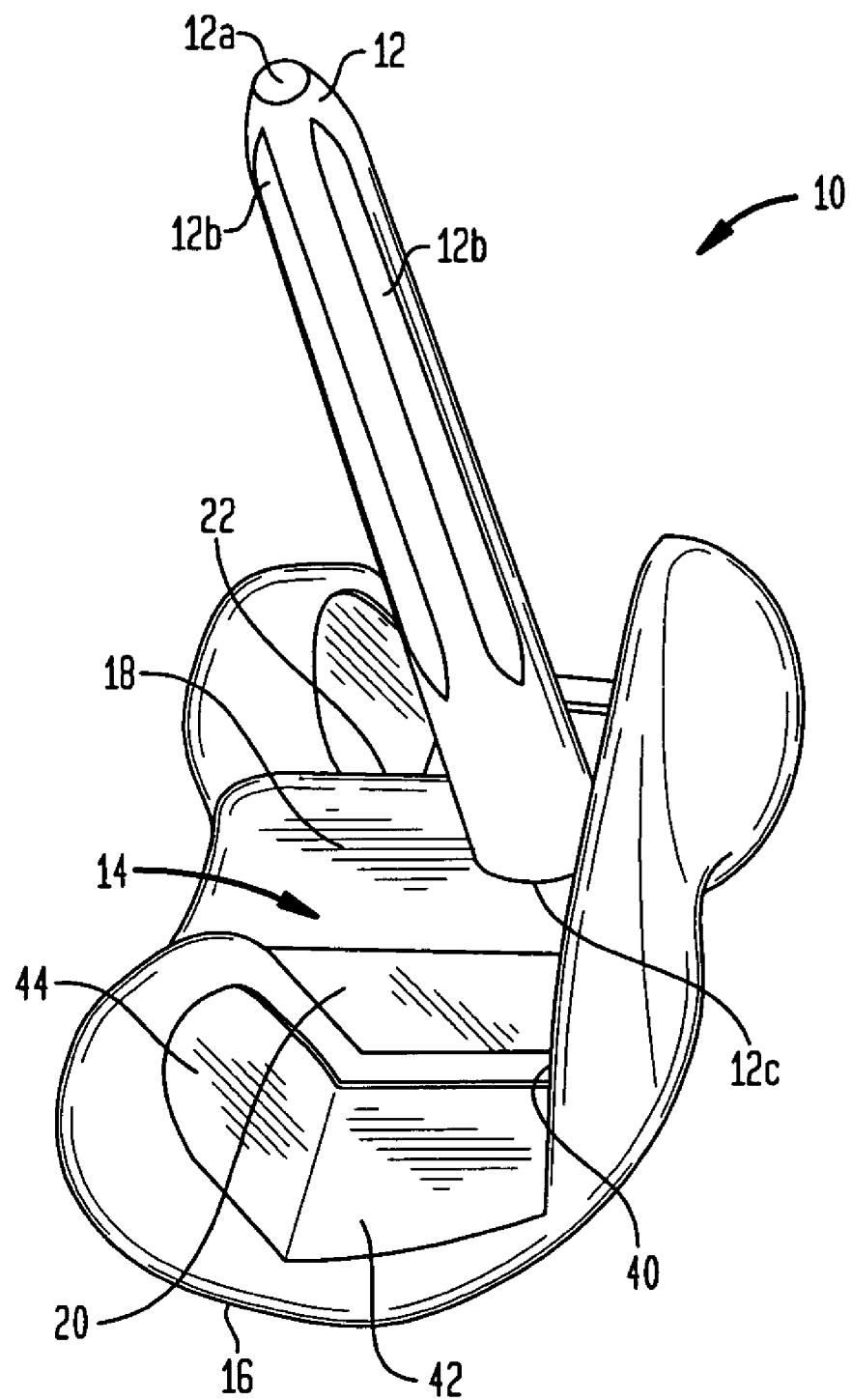
FIG. 1 is a perspective view of a femoral prosthetic or implant in accordance with one embodiment of the present invention.

Referring to the drawings wherein like reference numerals refer to like elements, there is shown in FIG. 1, in accordance with one embodiment of the present invention, an improved femoral prosthesis or implant designated generally by reference numeral 10. This implant 10 is preferably designed to cooperate and articulate with a tibial component in a reconstructed knee joint. In the embodiment shown in FIG. 1, implant 10 preferably includes a stem 12, a stabilizer box 14 and an articular surface 16. These elements are not unlike those found in a standard femoral prosthesis. The inclusion of stem 12 and stabilizer box 14 essentially makes implant 10 a total stabilized prosthesis for use in revision surgery, but it is to be understood that other embodiments in accordance with the present invention may employ different designs which may or may not include each of the components shown in the figures and discussed herein. For example, an implant in accordance with the present invention is not required to be a total stabilized knee prosthesis having a stem, stabilizer box and articular surface. Rather, other embodiments contemplate and implant which omits the stem and/or stabilizer box. Those of ordinary skill in the art would readily recognize the different modifications possible with the present invention.

Stem 12 preferably is an elongate structure adapted to be disposed within a previously reamed canal in the femur. This will be discussed further below in relation to the method of implanting implant 10. As is shown in the drawings, stem 12 may exhibit a tapered, substantially cylindrical structure, with sections of narrower diameter being situated closer to a first end 12a. This first end 12a (i.e.—the proximal end of stem 12) is the end which is ultimately placed furthest into the aforementioned femoral canal, and thus, this tapered design may aid in the placement of stem 12 therein. Of course, other stem designs are contemplated that do not employ such a tapered design. In addition, stem 12 may have one or more flutes 12b disposed at least partially along its length. Such flutes 12b, as shown in the drawings, are essentially rounded cut out sections that are designed to aid in fixably seating stem 12 within the femur. More particularly, as will be discussed more fully below, cement or the like is often injected into the femoral canal subsequent to placement of stem 12 therein. Flutes 12b preferably allow a stronger interface between stem 12, the cement and the bone. In other embodiments, flutes 12b may be many different shapes, may extend at various lengths along the length of the stem and may be completely omitted in the design. Finally, for clarification purposes, it is noted that stem 12 is preferably connected to box 14 at a second stem end 12c (i.e.—the distal end of stem 12). The connection between such components may be achieved in many different fashions. For example, in the preferred embodiment shown in the drawings, stem 12 is integrally formed with stabilizer box 14 at end 12c during the molding of implant 10. However, it is noted that stem 12 may be designed so as to be a modular portion of implant 10. In such a case, stem 12 is preferably removably attached to box 14 at second stem end 12c.

Figure 6:
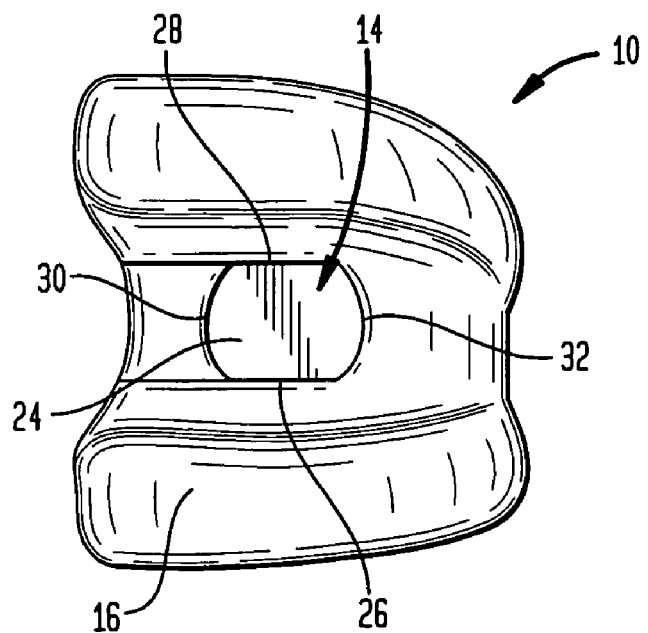
FIG. 6 is a bottom view of the femoral implant of FIG. 1.
Figure 7:
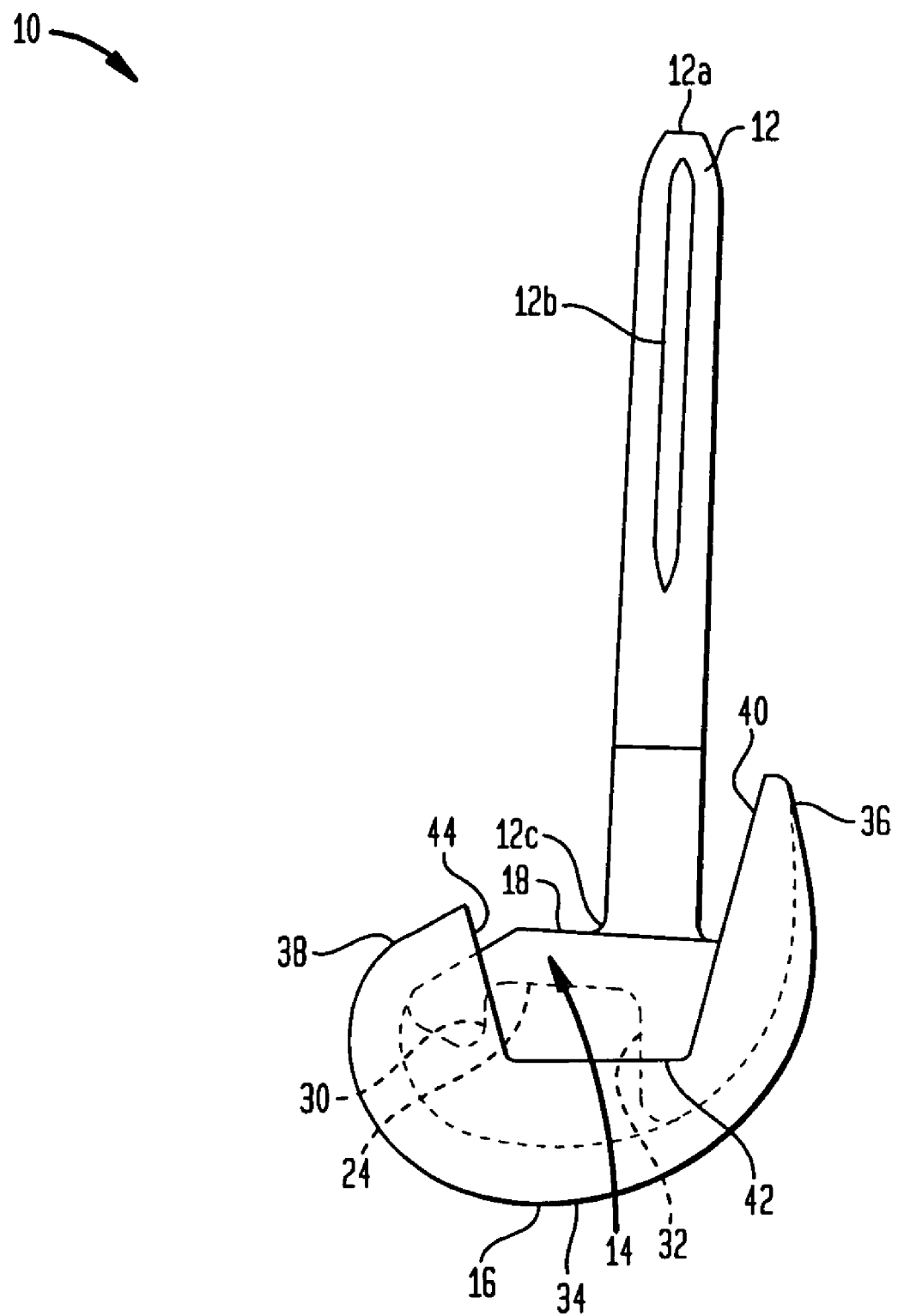
FIG. 7 is a cross sectional side view of a femoral implant of FIG. 1 through a center of the implant.

Stabilizer box 14 is, in fact, a box-like structure formed within implant 10, between stem 12 and articular surface 16. As is shown in the figures (FIGS. 1, 2 and 6 in particular), box 14 creates both distal and proximal surfaces on implant 10. Specifically, box 14 extends in the proximal direction from articular surface 16, thereby forming a box cut surface on the proximal side and a cam surface on the distal side. The box cut surface includes a top bone engaging surface 18 and two side bone engaging surfaces 20 and 22, and is designed to fit within a similarly shaped and sized cut out in the bone of the femur. Once again, this will be more fully discussed in relation to the method of implanting implant 10. This overall box cut surface preferably provides additional stability to the connection between implant 10 and the femur, as its cooperation with the cut out section prevents rotation and/or translation of implant 10 with respect to the femur. Similarly, the cam surface includes a cam platform 24 and four side walls 26, 28, 30 and 32 and is designed to cooperate with a post or like element situated on a tibial implant (not shown). This is similar to other total stabilized femoral implants, which are known in the art and designed to restore the stability lost with the removal of certain of the tendons and ligaments in the knee joint. Essentially, walls 26, 28, 30 and 32 form an enclosure (along with platform 24) that allows for a tibial post to extend into and move within the confines of same. This necessarily allows some movement of the tibial with respect to the femur, but also restricts movement in a similar fashion to the original tendons and ligaments. Although depicted as a substantially boxed shaped article, box 14 may employ other shapes as long as it is capable of cooperating with the bone of the femur and engaging a post of a counterpart tibial component to limit movement of the two components accordingly.

Figure 2:
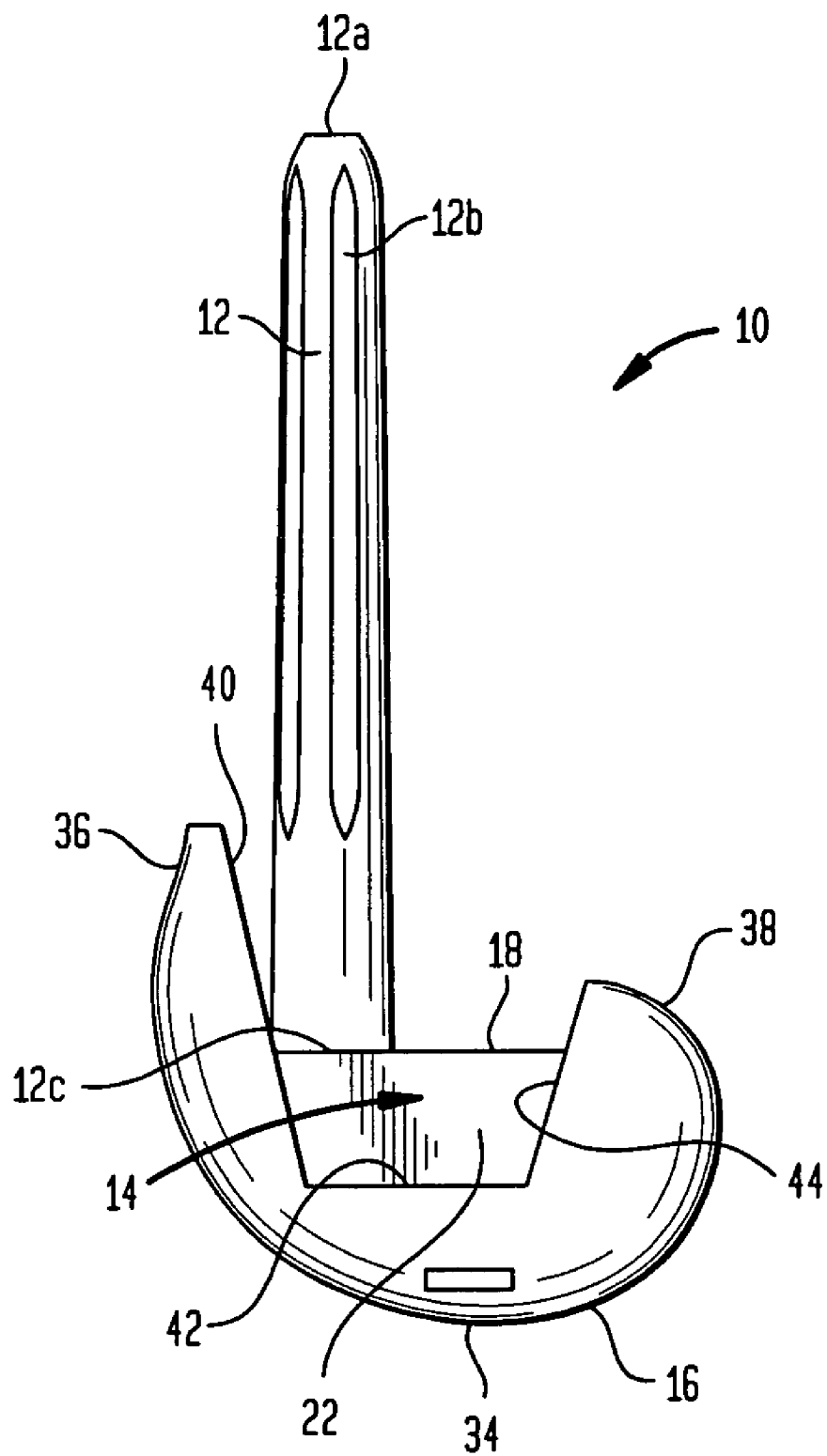
FIG. 2 is a side view of the femoral implant of FIG. 1.
Figure 3:
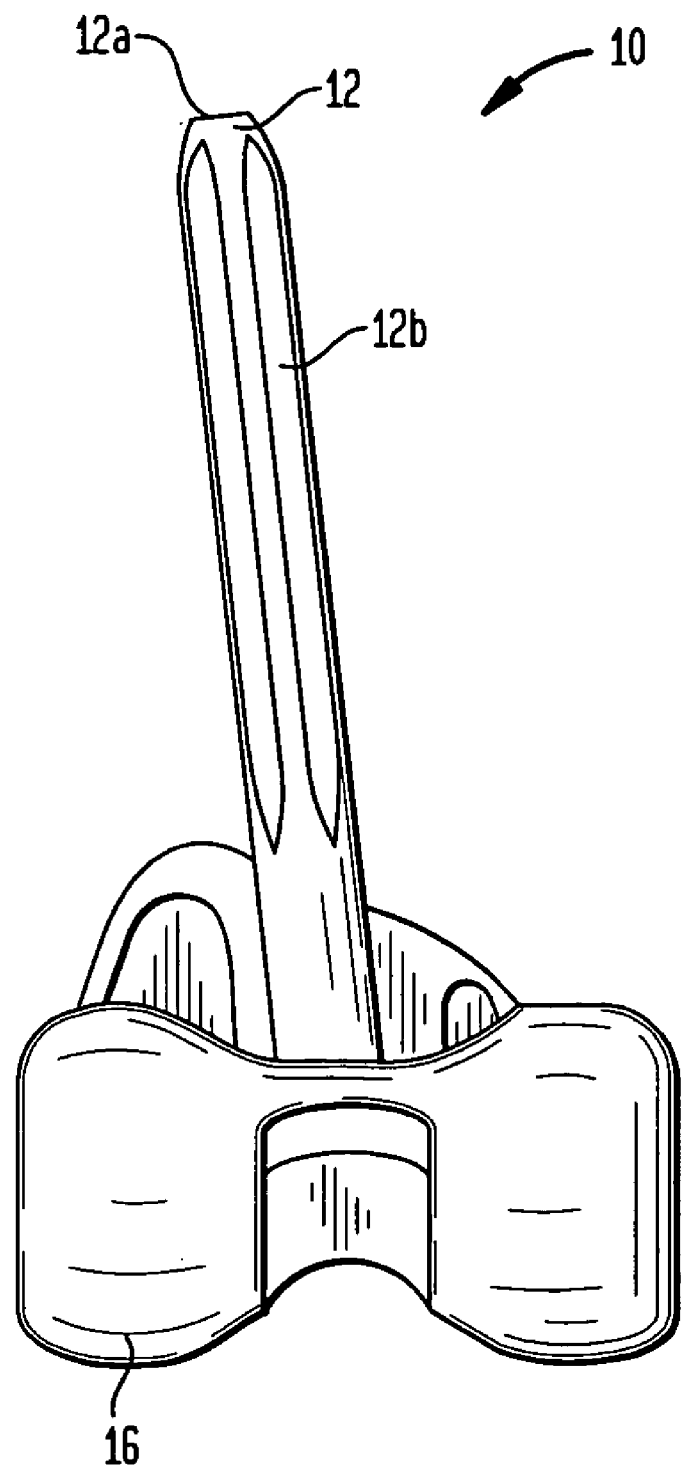
FIG. 3 is a rear view of the femoral implant of FIG. 1.
Figure 4:
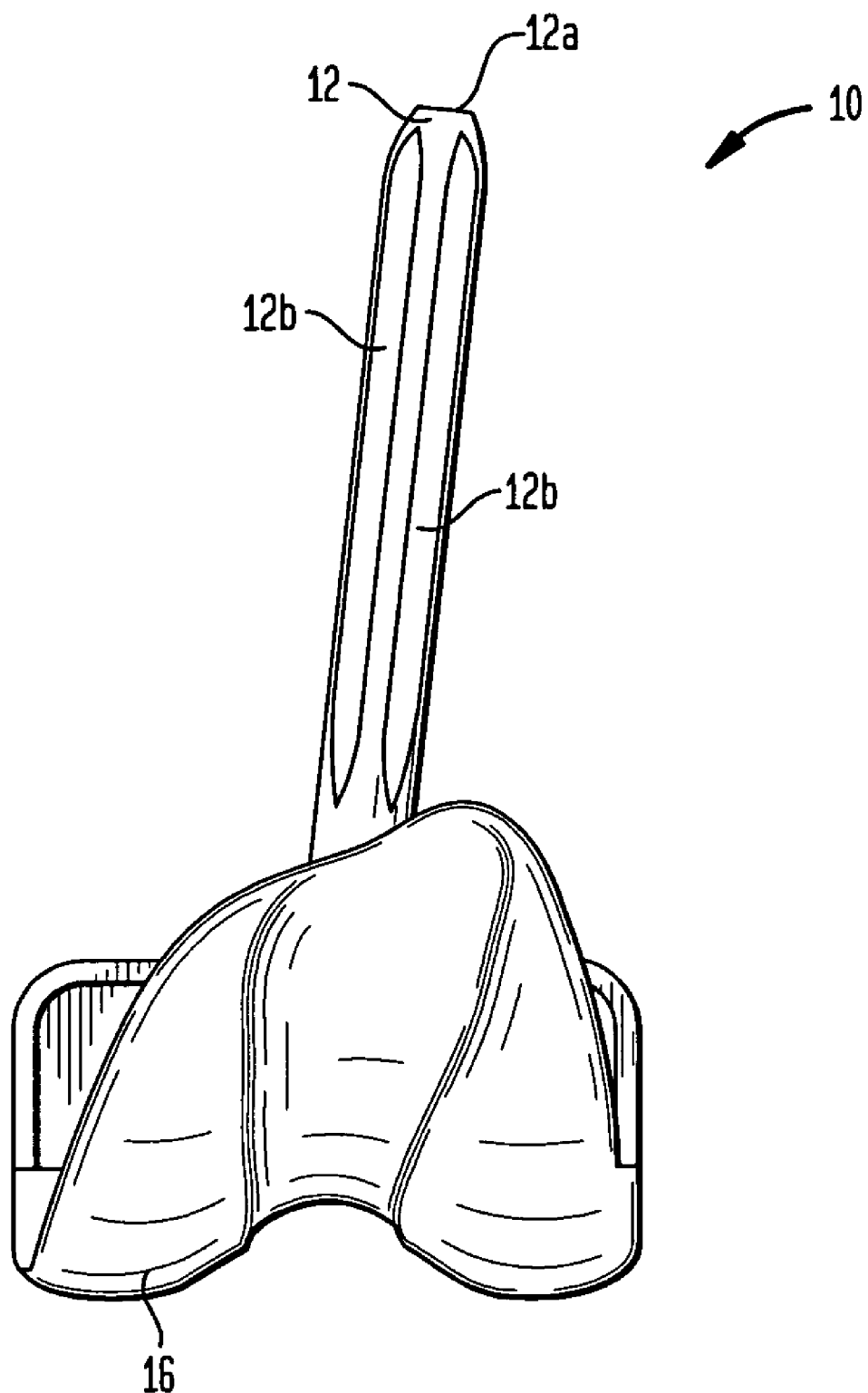
FIG. 4 is a front view of the femoral implant of FIG. 1.
Figure 5:
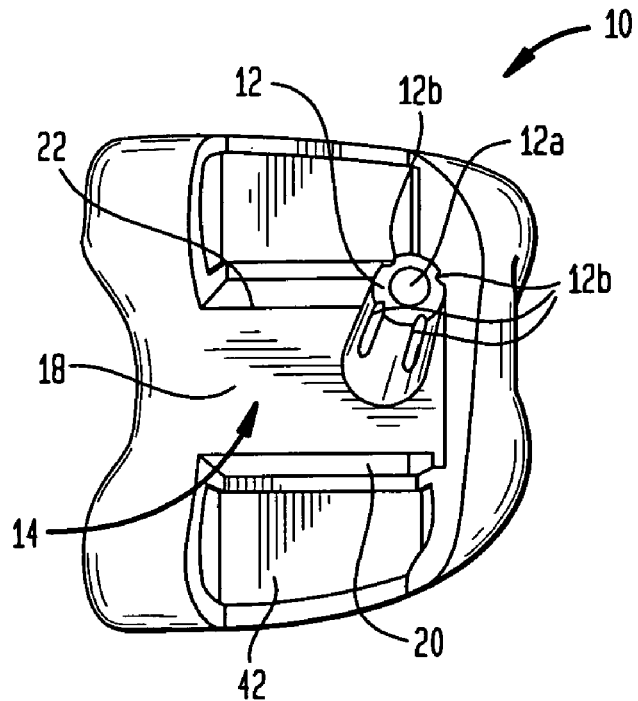
FIG. 5 is a top view of the femoral implant of FIG. 1.

Articular surface 16 preferably provides a surface capable of articulating with an articular surface of a suitable tibial component/implant (not shown). As is shown in the Figures, articular surface 16 is a generally curved surface extending from an anterior side to a posterior side of implant 10. However, such curve does not approximate that of a single arc of circle, but rather includes differently curved sections. In fact, as is best shown in FIG. 2, surface 16 may be further defined, no its distal side, by distal articular surface 34, anterior superior articular surface 36 and posterior superior articular surface 38. Additionally, on a proximal side of surface 16 is defined three different bone engaging surfaces for ultimately engaging cut surfaces of a femur. These three surfaces are situated across (from a medial to lateral side or vice versa) surface 16, but are split up by box 14. The three cut surface includes anterior surface 40, distal surface 42 and posterior surface 44. As such are adapted to engage like surfaces of the distal femur upon implantation, the proper preparation of the femur is vital before implanting implant 10. This will be discussed more fully below in connection with the method of implanting implant 10.

Figure 8:
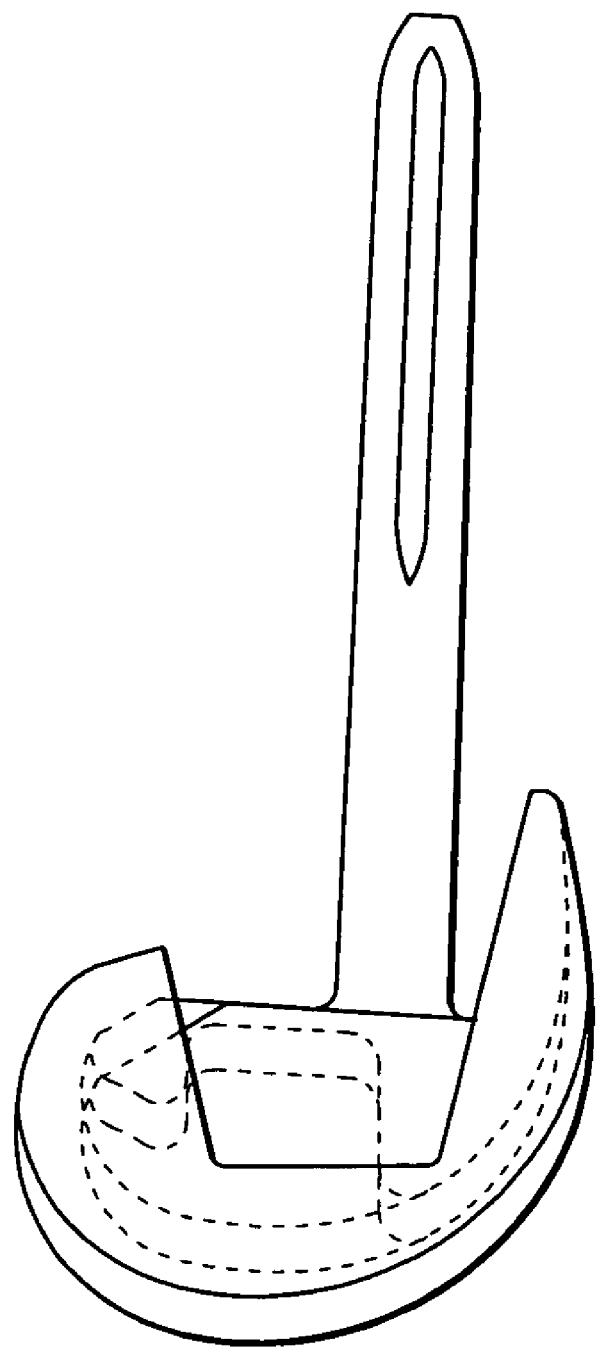
FIG. 8 is a cross sectional side view illustrating the relationship between different thickness implants in accordance with the embodiment depicted in FIG. 1, with the stems of the implants being aligned.
Figure 9:
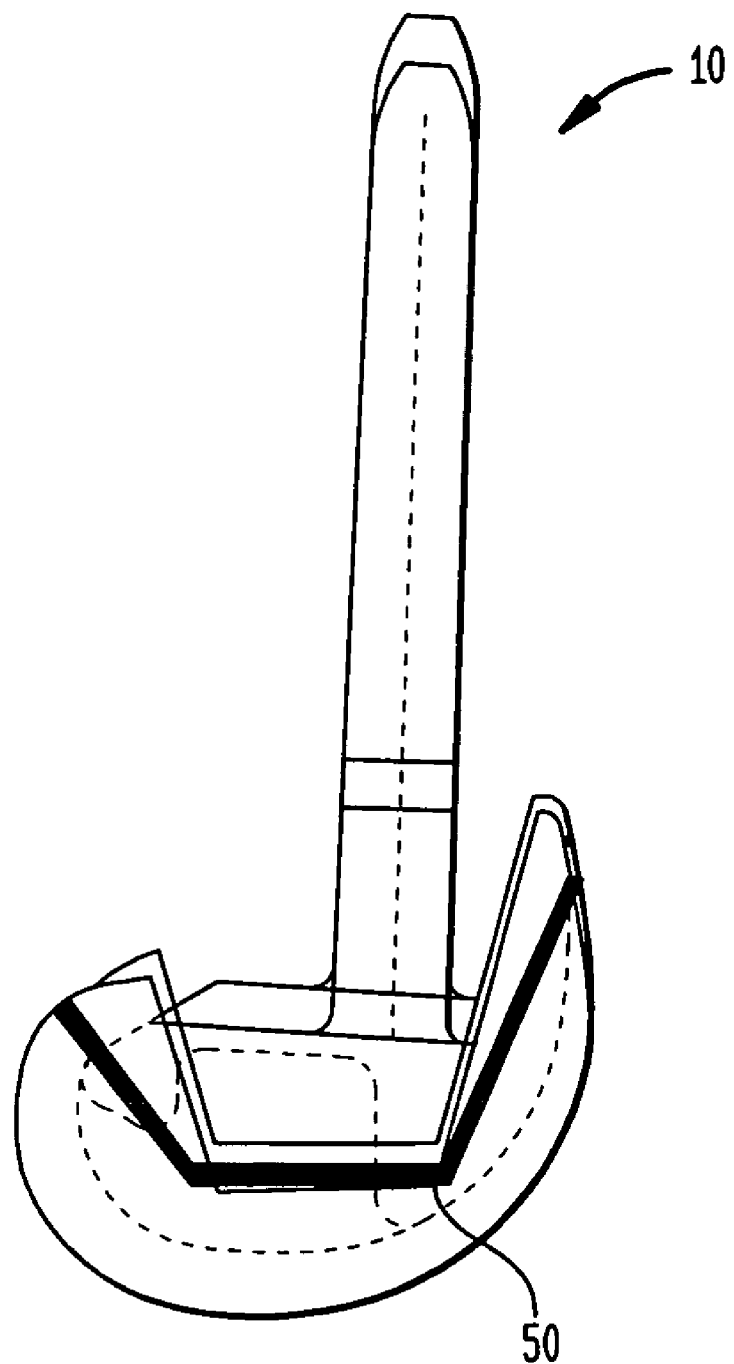
FIG. 9 is a cross sectional side view illustrating the relationship between different thickness implants in accordance with the embodiment depicted in FIG. 1, with the implants aligned along a mold parting line.

In accordance with the present invention, implant 10 may be designed with a varying distal thickness. Thus, a set of such implants may be provided for use in restoring the natural movement of the knee joint. Depending upon the amount of bone that has been removed from the femur in an initial surgery, or as a result of a revision surgery, a particular thickness may be selected. The design of implant 10 is such that varying the thickness of the prosthesis is possible, without greatly varying the different components of implant 10 or rendering the manufacture of such overly difficult. Specifically, implant 10 is configured with stem 12, the bone engaging surfaces of stabilizer box 14, anterior surface 40, distal surface 42, posterior surface 44, anterior superior articular surface 36 and posterior superior articular surface 38 remaining somewhat constant for each multiple condyle thickness implant, while the cam surfaces of stabilizer box 14 and distal articular surface 34 move distally away from such constant features. This enables the varying thickness of implant 10. FIG. 8 depicts a cross sectional view of a series of two implants in accordance with the present invention with their respective stems aligned, while FIG. 9 depicts a cross sectional view of the same two implants with their respective articular surfaces aligned. The relationship between the various components of such differing thickness implants in accordance with the present invention may best be garnered from these figures. Specifically, in accordance with the present invention, the bone engaging surfaces of stabilizer boxes 14 of a series of implants 10 are preferably such that all implants 10 in a series are designed to fit on similar bone cut surfaces. This means that varying thickness implants 10 may all be placed on the same prepared bone. It is simply up to the surgeon to decide which size to place thereon.

The invention of implant 10 allows for equal surface area contact between the bone of the femur and the prosthesis for multiple condyle thickness implants. This, unlike in typical augments, is accomplished by maintaining the same three cut bone engaging surfaces (anterior surface 40, distal surface 42 and posterior surface 44) and the same bone engaging surfaces (bone engaging surface 18, 20 and 22) of stabilizer box 14 for each size prosthesis. In addition, employing such elements reduces the reliance on the femoral stem to resist rotational loads during knee flexion, and the one-piece, monolithic stem feature allows for anatomical placement of implant 10. In essence, rather than varying all of the elements/components of implant 10, certain remain constant throughout the range of different implant sizes. This not only creates a simpler implant 10 to actually implant in a patient, but also one that is easy to manufacture. Both of these benefits will be discussed more fully below.

In use, depending upon the type of surgery being performed, the steps required in implanting implant 10 may vary. For example, an initial knee surgery would require initially shaping the bone of the femur. For the purposes of the description set forth herein, the method of implanting implant 10 will be described in connection with a revision knee surgery. In such a surgery, a surgeon would first preferably provide access to the knee joint through an incision or the like. Depending upon the particular surgical technique being employed, this may require a larger or smaller incision. For example, minimally invasive procedures would utilize one or more smaller incisions. Thereafter, the surgeon would preferably remove any previously implanted prosthesis, on both the femur and the tibia. This would leave exposed some previously shaped bone on both the tibia and femur which most likely requires additional shaping in order to remove degenerated portions and/or to properly cooperate with implant 10. Essentially, for the bone of the femur, such will need to be reshaped in order to allow cooperation with the three cut bone engaging surfaces (anterior surface 40, distal surface 42 and posterior surface 44) and the bone engaging surfaces (bone engaging surface 18, 20 and 22) of stabilizer box 14. This may involve cutting the bone to include surfaces which are mirror images of the surfaces of implant 10, and can be done through the use of a surgical saw or the like. Depending upon the previously implanted prosthesis, shaping the bone to properly engage box 14 may require the removal of a significant amount of bone.

In addition to shaping the bone to properly engage the three cut bone engaging surfaces (anterior surface 40, distal surface 42 and posterior surface 44) and the bone engaging surfaces (bone engaging surface 18, 20 and 22) of stabilizer box 14, the distal end of the femur must also be prepared to receive stem 12. Depending upon the previously implanted prosthesis, the femur may already include a canal formed therein which may only need to be cleaned out and possibly reshaped to accept stem 12. However, if the previous implant did not include a component similar to stem 12, the femur may need to be prepared in order to accept same. This may be accomplished through the use of a reamer or the like, as is known in the art. Once the femur is prepared to receive implant 10, a trial implant may be implanted onto the distal end of the femur. This trial implant or prosthesis preferably allows the surgeon or other medical professional to gauge the proper size for the final implant. Essentially, a trial implant is similar to a final implant, with certain steps during the manufacturing process possibly not being performed. Once the proper size is determined, implant 10 may be implanted. As is briefly mentioned above, cement or other adhesive may be employed to fixably attach implant 10 to the femur. However, such is not always necessary. In the case that it is, flutes 12b may aid in strengthening the cooperation between stem 12, the cement and the bone surface.

Once implant 10 is properly placed and fixed to the femur, the other prosthesis components of the knee joint may be implanted. For example, a counterpart tibial component may be placed on the proximal portion of the tibia, and allowed to articulate with implant 10. In this regard, it is to be understood that certain known tibial implants include one or more post-like structures that may cooperate with the cam surface of stabilizer box 14. Specifically, such a stabilizing post would preferably be disposed within the cavity formed by cam platform 24 and four side walls 26, 28, 30 and 32, upon full cooperation of implant 10 and the tibial implant. As is mentioned above, this type of cooperation approximates the restriction in motion typically provided by the various tendons and ligaments of the knee joint that may have been removed during the surgery. Thus, the implants utilized in this type of surgery not only replace the articulation surfaces of the knee joint, but also the structural integrity provided by other elements of the knee. Upon successful mating of the implants and subsequent to certain necessary balancing of the joint, the aforementioned incision may be closed and the surgery concluded. Of course, other methods steps may be included in the surgery, depending upon the particular surgical procedure being performed.

The manufacture of an implant 10 in accordance with the present invention may be accomplished by any known procedure. However, one such method is preferred and will be described herein. For example, often the manufacture of orthopedic implants may be accomplished through the use of molding processes, and implant 10 is no exception. Typically, such a process includes providing a mold that is capable of producing a wax model of the orthopedic article. Thereafter, such a wax model is made and coated with a ceramic material. After the ceramic material is allowed to set, the wax is melted away, thereby leaving a ceramic mold capable of withstanding the high temperatures needed to cast a metallic implant. Ultimately, metal is poured into this ceramic mold, allowed to cool and the ceramic material is chipped away. Subsequent to certain machining and smoothing processes, a suitable implant is created. A similar procedure may be utilized in conjunction with the manufacture of implant 10.

However, given the varying thickness capabilities of implant 10, the initial wax model creation may vary accordingly. The mold utilized in making such a wax model must be capable of varying depending upon the particular thickness implant 10 being manufactured. Specifically, the present invention allows for an efficient casting mold design that employs specific mold inserts for each multiple condyle thickness offering of a particularly sized implant 10. Such inserts each include structure utilized in molding stem 12, the three cut bone engaging surfaces (anterior surface 40, distal surface 42 and posterior surface 44), the bone engaging surfaces (bone engaging surface 18, 20 and 22) of stabilizer box 14, anterior superior articular surface 36 and posterior superior articular surface 38. As is shown in FIG. 9, these elements all sit above a mold parting line 50, which illustrates the line at which two pieces of the mold meet. In other words, in order to create differing thickness implants 10, a two piece mold is provided. The lower portion of the mold (below mold parting line 50) remains constant, while the upper portion varies according to the insert being employed. Any number of different inserts may be utilized to create any number of different thickness implants 10. Of course, once a proper wax model is created using such a mold, the remaining mold steps may be performed in accordance with that described above. It is also noted that some of the above-noted manufacturing steps may be omitted during the preparation of trial implants or the like.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A femoral trial prosthesis kit comprising:
at least a first and second femoral trial prosthesis, each femoral trial prosthesis including:
a stem having a proximal end and a distal end;
a stabilizer box integrally connected to the distal end of the stem; and
an articular surface integrally connected to the stabilizer box, the articular surface including an internal surface having an anterior bone engaging surface, a distal bone engaging surface, and a posterior bone engaging surface, and an external curved surface including a distal curved surface having a curvature between a most distant anterior point and a most distant posterior point and a posterior curved surface, wherein a distance between at least a portion of the distal bone engaging and distal curved surfaces of the first femoral trial prosthesis is less than a distance between at least a portion of the distal bone engaging and distal curved surfaces of the second femoral trial prosthesis, and wherein distances between the posterior bone engaging surface and the posterior curved surface, the curvature of the distal curved surfaces and distances between proximal ends of the stems and the distal bone engaging surfaces of the articular surfaces of the first and second femoral trial prostheses are substantially constant.

2. The femoral trial prosthesis kit according to claim 1, wherein the stems of the first and second femoral trial prosthesis are tapered.

3. The femoral trial prosthesis kit according to claim 1, wherein the stems of the first and second femoral trial prosthesis include flutes.

4. The femoral trial prosthesis kit according to claim 1, wherein the stems of the first and second femoral trial prosthesis are modular.

5. The femoral trial prosthesis kit according to claim 1, wherein the stabilizer boxes define a box cut surface on a proximal side and a cam surface on a distal side.

6. The femoral trial prosthesis kit according to claim 5, wherein the box cut surfaces include a top bone engaging surface and two side bone engaging surfaces.

7. The femoral trial prosthesis kit according to claim 5, wherein the cam surfaces include a cam platform and four side walls.

8. The femoral trial prosthesis kit according to claim 7, wherein the cam surfaces are adapted to cooperate with a portion of a tibial trial component.

9. The femoral trial prosthesis kit according to claim 1, wherein the external curved surface includes a distal curved surface, an anterior superior curved surface and a posterior curved surface.

10. The femoral trial prosthesis kit according to claim 9, wherein the distal curved surfaces of the external curved surfaces of the first and second trial prosthesis are substantially similar.

11. The femoral trial prosthesis kit according to claim 1, wherein the internal surfaces of the first and second trial prosthesis are substantially similar.

12. A femoral prosthesis kit comprising:
at least first and second femoral prostheses, each femoral prosthesis including:
a stem having a proximal end and a distal end;
a stabilizer box integrally connected to the distal end of the stem; and
an articular surface integrally connected to the stabilizer box, the articular surface including:
an internal bone engaging surface having a distal bone engaging surface and
an external curved surface having a distal curved surface having a curvature between a most distant anterior point and a most distant posterior point and a posterior curved surface,
wherein a distance between at least a portion of the distal bone engaging and the distal curved surfaces of the first femoral prosthesis is less than a distance between at least a portion of the distal bone engaging and the distal curved surfaces of the second femoral prosthesis, and the curvature of the distal curved surfaces and distances between proximal ends of the stems and the posterior curved surface of the first and second femoral prostheses are substantially constant.

13. The femoral prosthesis kit according to claim 12, wherein the distances between proximal ends of the stems and the distal bone engaging surfaces of the first and second femoral prostheses are substantially similar.

14. The femoral prosthesis kit according to claim 12, wherein the stabilizer boxes define a box cut surface on a proximal side and a cam surface on a distal side.

15. The femoral prosthesis kit according to claim 14, wherein the box cut surfaces include a top bone engaging surface and two side bone engaging surfaces.

16. The femoral prosthesis kit according to claim 14, wherein the cam surfaces include a cam platform and four side walls.

17. The femoral prosthesis kit according to claim 16, wherein the cam surfaces are adapted to cooperate with a portion of a tibial component.

18. The femoral prosthesis kit according to claim 12, wherein the external curved surfaces include a distal curved surface, an anterior superior curved surface and a posterior articular surface.

19. The femoral prosthesis kit according to claim 18, wherein the distal curved surfaces of the external curved surfaces of the first and second prosthesis are substantially similar.

20. The femoral prosthesis kit according to claim 12, wherein the internal surfaces of the first and second prosthesis are substantially similar.

21. A femoral prosthesis kit comprising:
   at least a first and second femoral prosthesis, each femoral prosthesis including:
   a stem having a proximal end and a distal end;
   a stabilizer box integrally connected to the distal end of the stem; and
   an articular surface integrally connected to the stabilizer box, the articular surface including:
   an internal bone engaging surface including a distal bone engaging surface and a posterior bone engaging surface and
   an external curved surface including a distal curved surface having a curvature between a most distant anterior point and a most distant posterior point and a posterior curved surface,
   wherein a distance between at least a portion of the distal bone engaging and the distal curved surfaces of the first femoral prosthesis is less than a distance between at least a portion of the distal bone engaging and the distal curved surfaces of the second femoral prosthesis, and wherein the curvature of the distal curved surfaces and the distances between at least a portion of the posterior bone engaging and the posterior curved surface of the first and second femoral prostheses are substantially constant.

22. The femoral prosthesis kit according to claim 21, wherein the distances between proximal ends of the stems and the distal bone engaging surface of the first and second femoral prostheses are substantially similar.

23. The femoral prosthesis kit according to claim 21, wherein the stabilizer boxes define a box cut surface on a proximal side and a cam surface on a distal side.

24. The femoral prosthesis kit according to claim 23, wherein the box cut surfaces include a top bone engaging surface and two side bone engaging surfaces.

25. The femoral prosthesis kit according to claim 23, wherein the cam surfaces include a cam platform and four side walls.

26. The femoral prosthesis kit according to claim 25, wherein the cam surfaces are adapted to cooperate with a portion of a tibial component.

27. The femoral prosthesis kit according to claim 21, wherein the external curved surfaces include a distal curved surface, an anterior superior curved surface and a posterior articular surface.

28. The femoral prosthesis kit according to claim 27, wherein the distal curved surfaces of the external curved surfaces of the first and second prosthesis are substantially similar.

29. The femoral prosthesis kit according to claim 21, wherein the internal surfaces of the first and second prosthesis are substantially similar.

* * * * *